(12) United States Patent
Fujii et al.

(10) Patent No.: US 6,632,338 B2
(45) Date of Patent: Oct. 14, 2003

(54) GAS SENSING ELEMENT INCORPORATED IN A GAS SENSOR FOR AN INTERNAL COMBUSTION ENGINE

(75) Inventors: Namitsugu Fujii, Yokkaichi (JP); Motoaki Satou, Kariya (JP); Kiyomi Kobayashi, Kuwana (JP); Yasumichi Hotta, Mie-ken (JP)

(73) Assignee: Denso Corporation, Aichi-Pref. (JP)

( * ) Notice: Subject to any disclaimer, the term of this patent is extended or adjusted under 35 U.S.C. 154(b) by 74 days.

(21) Appl. No.: 09/877,125

(22) Filed: Jun. 11, 2001

(65) Prior Publication Data
US 2002/0008025 A1 Jan. 24, 2002

(30) Foreign Application Priority Data

Jun. 12, 2000 (JP) .......................... 2000-175657
Mar. 26, 2001 (JP) ........................ 2001-088346

(51) Int. Cl.⁷ .............................................. G01N 27/41
(52) U.S. Cl. ...................... 204/429; 204/424; 204/428; 73/23.32
(58) Field of Search .............................. 204/429, 428, 204/424; 73/23.31, 23.32

(56) References Cited

U.S. PATENT DOCUMENTS

| 4,097,353 | A | | 6/1978 | Kishida et al. |
|---|---|---|---|---|
| 5,271,821 | A | | 12/1993 | Ogasawara et al. |
| 5,472,591 | A | * | 12/1995 | Saito et al. ................. 204/429 |
| 5,593,558 | A | * | 1/1997 | Sugino et al. .............. 204/429 |
| 5,766,434 | A | | 6/1998 | Fujii et al. |
| 5,849,165 | A | | 12/1998 | Kojima et al. |
| 6,447,658 | B1 | * | 9/2002 | Wu et al. .................... 204/424 |

FOREIGN PATENT DOCUMENTS

| JP | 61-153561 | 7/1986 |
|---|---|---|
| JP | 61-207961 | 9/1986 |
| JP | 1-227955 | 9/1989 |
| JP | 2-276956 | 11/1990 |
| JP | 10-221296 | 8/1998 |

* cited by examiner

Primary Examiner—Nam Nguyen
Assistant Examiner—Kaj K. Olsen
(74) Attorney, Agent, or Firm—Nixon & Vanderhye PC

(57) ABSTRACT

A second protective layer is a ceramic porous protective layer comprising coarse particles and fine particles structurally arranged in such a manner that interparticle cavities formed between the coarse particles are filled with the fine particles. At least either of the coarse particles and the fine particles contain at least one selected from the group consisting of γ-Al2O3, θ-Al2O3, δ-Al2O3 and solid solution having the same crystal structure as those of γ-Al2O3, θ-Al2O3, δ-Al2O3.

11 Claims, 4 Drawing Sheets

(×1000)

(×4000)

GAS SENSING ELEMENT INCORPORATED IN A GAS SENSOR FOR AN INTERNAL COMBUSTION ENGINE

BACKGROUND OF THE INVENTION

The present invention relates to a gas sensing element incorporated in a gas sensor used for controlling an air-fuel ratio of the gas mixture introduced into a combustion chamber of an internal combustion engine.

In an automotive vehicle, a gas sensor is provided in an exhaust pipe of an internal combustion engine to control the air-fuel ratio of the gas mixture introduced into a combustion chamber of the engine.

For example, a practical gas sensing element incorporated in the gas sensor is required to detect a concentration of oxygen gas contained in the exhaust gas. The gas sensing element may be formed by a ZrO2 solid electrolytic body which is capable of generating an electromotive force in accordance with the oxygen concentration.

Japanese Patent No. HEI 2-15017 discloses a conventional gas sensing element whose output is responsive to an electromotive force.

According to this type of conventional oxygen concentration detector, a gas sensing element is provided at a distal end of this detector. The gas sensing element is configured into a cup-shaped multilayered structure comprising a reference gas sensing electrode, a solid electrolytic sintered body, a measured gas sensing electrode, and an electrode protective layer which are successively stacked in this order. A heater is accommodated in an inside chamber of the cup-shaped sensing element.

The electrode protective layer is a ceramic coating layer, or a double layer consisting of a ceramic coating layer and a γ-Al2O3 layer provided on this ceramic coating layer.

Exhaust gas reaches the measured gas sensing electrode through the ceramic coating layer or the double layer of the ceramic coating layer and the γ-Al2O3 layer.

Recently enacted regulations relating to exhaust gas emissions have forced automotive manufacturers to develop automotive engines having the capability of precisely controlling the combustion. To realize this, it is essentially important to provide an excellent gas sensor having sensing properties stable under severe exhaust gas temperatures and durable for a long time.

One of the main factors causing change in sensing properties is deterioration of the gas sensing element subjected to poisonous substances such as Pb, S etc. contained in gasoline, additives K, Na, P, Ca, Zn etc. involved in gasoline or oil and the Si component contained in a seal member of the internal combustion engine.

U.S. Pat. No. 5,766,434 (corresponding to JP10-221296) proposes a gas sensing element comprising a measured gas sensing electrode covered by a protective layer including coarse particles and fine particles structurally arranged in such a manner that interparticle cavities formed between the coarse particles are filled with the fine particles.

This conventional technique intends to adequately set a porosity and a pore diameter of the protective layer by filling the coarse interparticle cavities with the fine particles. Anti-poisoning properties can be improved. Obtained gas choking effect will cause unburnt components in the exhaust gas to react with residual oxygen in an equilibrium condition. The waveform of a sensor output will be sharpened.

The above-described prior art effectively prevents blinding or plugging of the protective layer subjected to crystalline or glass substances formed by gasoline or oil compounds. Accordingly, the gas sensing element can be effectively protected from poisonous substances.

However, the above-described prior art cannot bring satisfactory effects against poisonous substances of gas phase, such as Si components, contained in the seal member or the like of the internal combustion engine.

Poisoning mechanism of Si components is as follows.

Si components of gas phase residing in the vicinity of a gas sensing element penetrate the protective layer and subsequently reach the measured gas sensing electrode. The measured gas sensing electrode, when covered by Si components, loses its activity. As a result, Si components deteriorate the sensing properties of the gas sensing element.

SUMMARY OF THE INVENTION

In view of the above-described problems, the present invention has an object to prevent poisonous substances, such as gaseous Si components, from reaching the measured gas sensing electrode. In other words, an object of the present invention is to prevent the measured gas sensing electrode from being covered by poisonous substances. Thus, the present invention provides a gas sensing element capable of maintaining a stable sensor output for a long term.

To accomplish the above and other related objects, the present invention provides a first gas sensing element comprising a solid electrolytic body, a reference gas sensing electrode provided on a surface of the solid electrolytic body so as to be exposed to a reference gas, and a measured gas sensing electrode provided on another surface of the solid electrolytic body so as to be exposed to a measured gas. A ceramic porous protective layer is provided on a surface of the measured gas sensing electrode. The protective layer comprises coarse particles and fine particles structurally arranged in such a manner that inter particle cavities formed between the coarse particles are filled with the fine particles. And, at least either of the coarse particles and the fine particles contain at least one selected from the group consisting of γ-Al2O3, θ-Al2O3, δ-Al2O3 and solid solution having the same crystal structure as those of γ-Al2O3, θ-Al2O3, and δ-Al2O3.

The first gas sensing element of the present invention is characterized in that at least either of the coarse particles and the fine particles constituting the protective layer contain at least one selected from the group consisting of γ-Al2O3, θ-Al2O3, δ-Al2O3 and solid solution having the same crystal structure as those of γ-Al2O3, θ-Al2O3, δ-Al2O3. More specifically, the solid solution is an alumina solid solution having the crystal structure of either a tetragonal system or a monoclinic system which are the same crystal structures as those of γ-Al2O3, θ-Al2O3, δ-Al2O3.

The coarse particles and the fine particles can be made of the same material or can be made of different materials.

For example, practical examples of the solid solution are γ-$(Al_{1-x}La_x)_2O_3$, θ-$(Al_{1-x}La_x)_2O_3$, and δ-$(Al_{1-x}La_x)_2O_3$.

The protective layer covers the entire surface of the measured gas sensing electrode. It is also possible to provide the protective layer so as to cover the surface of the solid electrolytic body together with the measured gas sensing electrode.

Furthermore, it is possible to provide another layer between the protective layer and the measured gas sensing electrode (refer to FIG. 1).

Effects of the first gas sensing element of the present invention will be explained hereinafter.

The protective layer of the first gas sensing element consists of coarse particles and fine particles. Accordingly, interparticle cavities formed between the coarse particles are filled with the fine particles. It becomes possible to sufficiently reduce a porosity and a pore diameter of the protective layer.

Furthermore, in a process of forming the protective layer, the coarse particles cooperatively constitute bridges which effectively prevent generation of cracks in the protective layer. Thus, the present invention makes it possible to easily obtain a protective layer having a satisfactory thickness.

The coarse particles and fine particles constituting the protective layer contain a material having a large specific surface, such as γ-Al2O3, θ-Al2O3, and δ-Al2O3.

Accordingly, it becomes possible to enlarge a substantial contact area of the protective layer to be exposed to poisonous gaseous substances. Thus, the protective layer surely traps the poisonous substances.

In this manner, the present invention provides a protective layer which can surely trap incoming poisonous gaseous substances, thereby surely preventing the poisonous substances from reaching the measured gas sensing electrode.

Hence, it becomes possible to maintain a stable sensor output for a long time.

As described above, the present invention can provide a gas sensing element which is capable of preventing poisonous gaseous substances, such as Si components, from reaching the measured gas sensing electrode, and is accordingly capable of preventing the measured gas sensing electrode from being covered by the poisonous gaseous substances, and therefore capable of maintaining a stable sensor output for a long time.

Thus, the present invention provides a gas sensing element preferably installable in an exhaust system of an internal combustion engine.

It is preferable that the alumina material constituting the protective layer, such as γ-Al2O3, θ-Al2O3, and δAl2O3 or solid solution having the same crystal structure as those of γ-Al2O3, θ-Al2O3, and δ-Al2O3 has a specific surface equal to or larger than 50 m$^2$/g. The effect of this invention can thereby be enhanced.

If the specific surface of the alumina material or relevant solid solution is smaller than 50 m$^2$/g, the ability of trapping poisonous materials of individual particles will be dissatisfactory and therefore the sensor will suffer from the shortage of poisonous substance trapping capability.

It is preferable that the protective layer has a thickness equal to or larger than 50 µm. This makes sure that the poisonous substances can be sufficiently brought into contact with the particles of γ-Al2O3 or the like. Thus, the sensor performance can be improved so as not to be adversely influenced by poisonous substances.

If the thickness of the protective layer is smaller than 50 µm, the poisonous substances will not be sufficiently trapped by the particles. Hence, the sensor capability of trapping poisonous substances will be worsened.

Application of the present invention is not limited to a cup-shaped gas sensing element shown in FIG. 1. Therefore, the present invention can be applied to other types of gas sensing elements, such as a multilayered planar gas sensing element.

Furthermore, the gas sensor of the present invention can be used as an oxygen sensor or an air-fuel ratio sensor installed in an automotive internal combustion engine, or as a NOx sensor, a CO sensor, a HC sensor of a multilayered type.

According to the present invention, it is preferable that the protective layer contains a noble metallic catalyst.

In general, noble metallic catalysts equilibrate unburnt gas and accordingly have a function of stabilizing a sensor output. In other words, the noble metallic catalyst assists or improves the ability of trapping poisonous gaseous substances in the protective layer. Thus, the effect of the present invention can be further enhanced.

Furthermore, as described later with reference to FIG. 5, it is preferable that the noble metallic catalyst is disposed in a discrete manner around coarse particles or between fine particles.

For example, the noble metallic catalyst is Pt, Rh, Pd etc.

Furthermore, it is preferable that an amount of the noble metal contained in the protective layer is in a range from 0.1% to 5%.

This ensures the gas equilibrating function of the noble metal, thereby further enhancing the sensor capability of trapping poisonous substances.

If the content of the noble metal is less than 0.1%, the effect of the present invention will not be obtained. If the content of the noble metal exceeds 5%, an adsorbing time of the noble metal required to adsorb the gas components will be fairly extended in a process of equilibrating the unburnt gas and the residual oxygen. This will worsen the sensor response, even through the poisonous substance trapping capability may be adequately maintained.

Furthermore, according to the present invention, it is preferable that the protective layer satisfies a relationship that a ratio RB/RA is equal to or larger than 3, where RA represents an average particle diameter of the fine particles while RB represents an average particle diameter of the coarse particles.

When the ratio RB/RA is equal to or larger than 3, the interparticle cavities formed between the coarse particles are efficiently filled with the fine particles. The porosity and the pore diameter of the protective layer can be reduced adequately. The poisonous substance trapping capability can be enhanced.

If the ratio RB/RA is smaller than 3, it will become difficult to sufficiently fill the interparticle cavities formed between the coarse particles with the fine particles. The poisonous substance trapping capability will be deteriorated.

Furthermore, it is preferable that an upper limit of RA/RB is set to 150 in view of stability of a slurry used to form the protective layer.

Furthermore, according to the present invention, it is preferable that an average particle diameter of the fine particles is in a range from 0.1 µm to 5 µm and an average particle diameter of the coarse particles is in a range from 0.3 µm to 50 µm. This is effective to obtain a protective layer having an excellent poisonous substance trapping capability.

If the average particle diameter of the fine particles is less than 0.1 µm, cracks will be caused in the process of forming the protective layer. The poisonous substance trapping effect will be lowered. If the average particle diameter of the fine particles exceeds 5 µm, dispersion of slurry particles used to form the protective layer will be no good. Thus, it will be difficult to obtain a homogeneous protective layer. The poisonous substance trapping effect will be lowered.

Similarly, if the average particle diameter of the coarse particles is less than 0.3 µm, cracks will be caused in the process of forming the protective layer. The poisonous substance trapping effect will be lowered. If the average particle diameter of the coarse particles exceeds 50 µm, dispersion of slurry particles used to form the protective layer will be no good. Thus, it will be difficult to obtain a homogeneous protective layer. The poisonous substance trapping effect will be lowered.

Next, according to the present invention, it is preferable that the protective layer satisfies a relationship that a weight ratio WA/W is equal to or larger than 20, wherein W is a sum of WA and WB (i.e., W=WA+WB), WA represents an amount of the fine particles contained in the protective layer, and WB represents an amount of the coarse particles contained in the protective layer.

When the weight ratio WA/W is equal to or larger than 20, the interparticle cavities formed between the coarse particles are efficiently filled with the fine particles. The porosity and the pore diameter of the protective layer can be reduced adequately. The poisonous substance trapping capability can be enhanced.

If the weight ratio WA/W is excessively large, the efficiency of filling the coarse interparticle cavities with the fine particles will be worsened. A preferable upper limit of the weight ratio WA/W is 50.

Furthermore, the present invention provides a second gas sensing element comprising a solid electrolytic body, a reference gas sensing electrode provided on a surface of the solid electrolytic body so as to be exposed to a reference gas, a measured gas sensing electrode provided on another surface of the solid electrolytic body so as to be exposed to a measured gas. A ceramic porous protective layer is provided on a surface of the measured gas sensing electrode. The protective layer comprises coarse particles and fine particles arranged in such a manner that interparticle cavities formed between the coarse particles are filled with the fine particles. And, at least either of the coarse particles and the fine particles have a specific surface equal to or larger than 50 $m^2/g$.

The protective layer of the second gas sensing element of the present invention consists of coarse particles and fine particles. Accordingly, the interparticle cavities formed between the coarse particles are filled with the fine particles. It becomes possible to sufficiently reduce a porosity and a pore diameter of the protective layer.

Furthermore, in a process of forming the protective layer, the coarse particles cooperatively constitute bridges which effectively prevent generation of cracks in the protective layer. Thus, the present invention makes it possible to easily obtain a protective layer having a satisfactory thickness.

The coarse particles and fine particles constituting the protective layer contain a material having a large specific surface.

Accordingly, it becomes possible to enlarge a substantial contact area of the protective layer to be exposed to poisonous substances of gas phase. Thus, the protective layer surely traps the poisonous substances.

In this manner, the present invention provides a protective layer which can surely trap incoming poisonous gaseous substances, thereby surely preventing the poisonous substances from reaching the measured gas sensing electrode.

Hence, it becomes possible to maintain a stable sensor output for a long time.

If the specific surface is less than 50 $m^2/g$, the ability of trapping poisonous materials of individual particles will be dissatisfactory and therefore the sensor will suffer from the shortage of poisonous substance trapping capability.

As described above, the present invention can provide a gas sensing element which is capable of preventing poisonous gaseous substances, such as Si components, from reaching the measured gas sensing electrode, and accordingly capable of preventing the measured gas sensing electrode from being covered by the poisonous substances of gas phase, and therefore capable of maintaining a stable sensor output for a long time.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
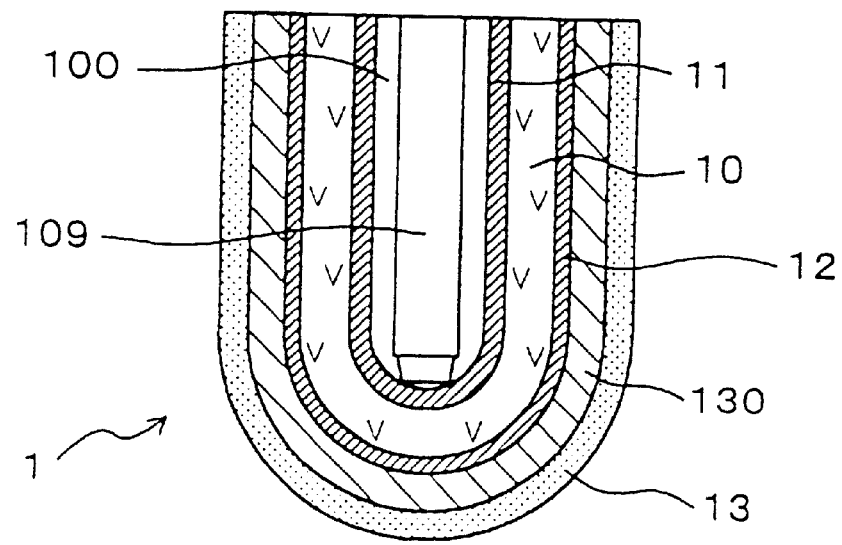
FIG. 1 is a cross-sectional view showing an essential arrangement of a gas sensing element in accordance with a first embodiment of the present invention.

Preferred embodiments of the present invention will be explained hereinafter with reference to attached drawings. Identical parts are denoted by the same reference numerals throughout the drawings.

First Embodiment

Hereinafter, a gas sensing element according to a preferred embodiment of the present invention will be explained with reference to FIGS. 1 to 3.

As shown in FIG. 1, the gas sensing element 1 of this embodiment comprises a cup-shaped solid electrolytic body 10 with one end closed and the other end opened, a reference gas sensing electrode 11 provided on an inner surface of the solid electrolytic body 10 so as to be exposed to a reference gas, and a measured gas sensing electrode 12 provided on an outer surface of the solid electrolytic body 10 so as to be exposed to a measured gas.

A first protective layer 130, coated by plasma spray, is provided on the surface of the measured gas sensing electrode 12. A second protective layer 13, made of a ceramic porous member, is provided on the surface of the first protective layer 130. The second protective layer 13 comprises coarse particles 131 and fine particles 132 structurally arranged in such a manner that interparticle cavities formed between the coarse particles 131 are filled with the fine particles 132, as shown in FIG. 2.

The coarse particles 131 and the fine particles 132, cooperatively constituting the second protective layer 13, contain at least one selected from the group consisting of γ-Al2O3, θ-Al2O3, δ-Al2O3 and solid solution having the same crystal structure as those of γ-Al2O3, θ-Al2O3, δ-Al2O3.

Hereinafter, this embodiment will be explained in more detail.

The gas sensing element 1 of this embodiment is incorporated in a gas sensor 2 installed in an exhaust gas passage of an automotive engine. An output of the gas sensing element 1 is utilized to control the air-fuel ratio of the engine.

The gas sensing element 1 of this embodiment comprises the solid electrolytic body 10 having an oxygen ionic conductance, the reference gas sensing electrode 11, and the measured gas sensing electrode 12 which cooperatively constitute an electrochemical cell. Air, serving as the reference gas, is introduced in the cup-shaped solid electrolytic body 10. An electric potential difference, representing an oxygen concentration difference between the reference gas and the measured gas, is produced between the gas sensing electrode 11 and the measured gas sensing electrode 12. In this respect, the gas sensing element 1 is a cell producing an electromotive force representing the oxygen concentration in the exhaust gas.

The second protective layer 13 covers the outer surface of the first protective layer 130. The inside space of the solid electrolytic body 10 defines a reference gas chamber 100 which is filled with air. A rodlike ceramic heater 109 is placed in the reference gas chamber 100.

Figure 2:
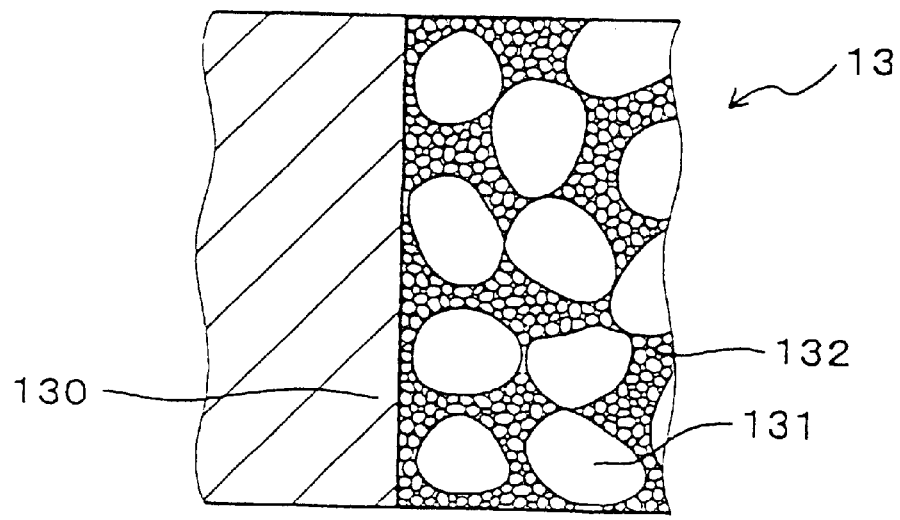
FIG. 2 is an enlarged view showing details of a second protective layer in accordance with the first embodiment of the present invention.

As shown in FIG. 2, the second protective layer 13 is a porous layer consisting of coarse particles 131 and fine particles 132. Each of the coarse particles 131 and the fine particles 132 is made of metallic oxide which is thermally stable. The coarse particles 131 and the fine particles 132 are continuously connected to form the second protective layer 13.

The second protective layer 13 of this embodiment was fabricated in the following manner.

The coarse particles 131 made of α-Al2O3 and the fine particles 132 made of γ-Al2O3 were prepared. An average particle diameter of the coarse particles 131 is 15 μm, and an average particle diameter of the fine particles 132 is 0.2 μm.

Water, inorganic binder and dispersant were added to the prepared particles to fabricate a slurry. The weight percentage of inorganic binder relative to all of the particles is 3 to 10 wt %. This slurry was applied or coated on the surfaces of the solid electrolytic body 10 and the measured gas sensing electrode 12 by dipping or spraying. The used inorganic binder is alumina sol, and the dispersant is aluminum nitrate.

Thereafter, the applied slurry was baked at the temperature range of 500° C. to 900° C. to obtain the second protective layer 13.

Figure 4A:
FIGS. 4A and 4B are photographic drawings (magnifications: ×1,000 and ×4,000) showing details of the second protective layer in accordance with the first embodiment of the present invention.
Figure 4B:

FIGS. 4A and 4B show SEM (scanning electron microscopic) images of a cross section (i.e., cut surface) of the obtained second protective layer 13. According to the SEM image shown in FIG. 4A, it is observed that interparticle cavities formed between the coarse particles 131 are filled with the fine particles 132. FIG. 4B, which is an enlarged view of FIG. 4A, more clearly shows the structural features of the present invention. Namely, the interparticle cavities formed between the coarse particles 131 are filled with the fine particles 132.

Accordingly, it is confirmed that the above-described fabricating method realizes the characteristic structure that the interparticle cavities formed between the coarse particles 131 are filled with the fine particles 132.

The gas sensor incorporating the gas sensing element 1 of this embodiment will be explained hereinafter.

Figure 3:
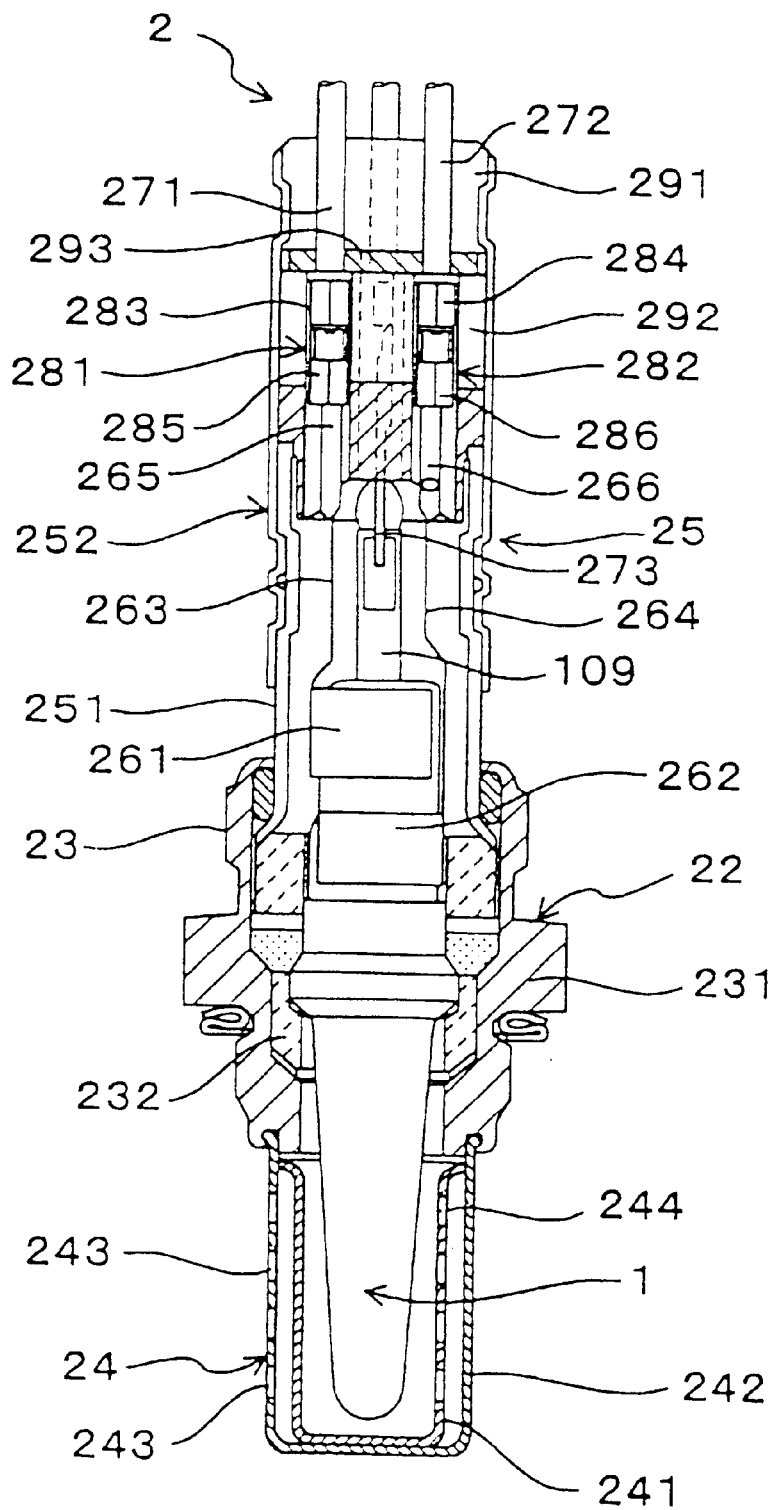
FIG. 3 is a cross-sectional view showing a gas sensor in accordance with the first embodiment of the present invention.

As shown in FIG. 3, the gas sensor 2 has a housing 22 which accommodates the gas sensing element 1 of this embodiment.

The housing 22 has a barrel portion 23 with a flange 231 formed at the center thereof. An exhaust cover 24, to be placed in an exhaust gas passage, is connected to the lower end of the barrel portion 23. An air cover 25, to be exposed to the air, is connected to the upper end of the barrel portion 23.

The exhaust cover 24 consists of an inner cover 241 and an outer cover 242 both of which are made of stainless steel. These covers 241 and 242 have a plurality of holes 243 opened to introduce the exhaust gas into the exhaust cover 24.

On the other hand, the air cover 25 comprises a main cover 251 attached at its one end (i.e., its lower end) to the barrel portion 23 and a sub cover 252 overlapping with the other end (i.e., an upper end) of the main cover 251. These covers 251 and 252 have holes for introducing air into the air cover 25.

The gas sensing element 1 is supported through an insulating member 232 by the inside surface of the barrel portion 23. A metallic plate terminal 261 is connected to a terminal electrode (not shown) extending from the reference gas sensing electrode 11 of the gas sensing element 1. Another metallic plate terminal 262 is connected to a terminal electrode (not shown) extending from the measured gas sensing electrode 12 of the gas sensing element 1.

The plate terminals 261 and 262 are connected to output lead wires 271 and 272. More specifically, belt-like terminal pieces 263 and 264 protrude from the plate terminals 261 and 262 toward contact pieces 265 and 266, respectively.

The terminal pieces 263 and 264 are connected to lower ends 285 and 286 of connectors 281 and 282. The other ends 283 and 284 of the connectors 281 and 282 are connected to the output lead wires 271 and 272.

The plate terminals 261 and 262 are respectively formed by deforming an inverse T-shaped metallic plate into a cylindrical shape so as to hold the above-described terminal electrodes. An elastic spring force of the metallic plate gives an adequate pressing force for clamping the terminal electrodes by the plate terminals 261 and 262.

The lead wires 271 and 272 are respectively subjected to a tensile force acting in an axial direction of the gas sensor 2. Thus, the lead wires 271 and 272 may pull the plate terminals 261 and 262 via the connectors 281 and 282, respectively. Thus, the plate terminals 261 and 262 may slide in the axial direction.

A stopper 293, sandwiched between rubber bushes 291 and 292, is provided at the upper end of the gas sensor 2 to restrict the sliding of the plate terminals 261 and 262. The stopper 293, also preventing the shifting of connectors 281 and 282, is a resin-made member capable of insulating the lead wires 271 and 272 from each other.

A wire 273 supplies electric power to a heater 109 of the gas sensing element 1. The gas sensor 2 is fixed at the flange 231 to the wall of the exhaust passage so that the exhaust cover 24 protrudes in the exhaust gas passage.

Hereinafter, functions and effects of this embodiment will be explained.

The second protective layer 13 of this embodiment consists of the coarse particles 131 and the fine particles 132.

The interparticle cavities formed between the coarse particles 131 are filled the fine particles 132 so that the porosity and the pore diameter of the protective layer 13 can be sufficiently reduced.

Furthermore, in the process of forming the second protective layer 13, the coarse particles 131 cooperatively constitute bridges which effectively prevent generation of cracks in the protective layer 13. Thus, it becomes possible to easily obtain the protective layer 13 having a satisfactory thickness.

The coarse particles 131 and the fine particles 132 constituting the second protective layer 13 contain a material having a large specific surface, such as $\gamma$-Al2O3, $\theta$-Al2O3, and $\delta$-Al2O3 or solid solution having the same crystal structure as those of $\gamma$-Al2O3, $\theta$-Al2O3, $\delta$-Al2O3.

Accordingly, it becomes possible to enlarge a substantial contact area of the second protective layer 13 to be exposed to poisonous gaseous substances. Thus, the second protective layer 13 surely traps the poisonous substances.

In this manner, the second protective layer 13 can surely trap incoming poisonous gaseous substances, thereby surely preventing the poisonous substances from reaching the measured gas sensing electrode.

Hence, it becomes possible to maintain a stable sensor output for a long time.

As described above, the first embodiment can provide a gas sensing element which is capable of preventing poisonous gaseous substances, such as Si components, from reaching the measured gas sensing electrode, and accordingly is capable of preventing the measured gas sensing electrode from being covered by the poisonous gaseous substances, and is therefore capable of maintaining a stable sensor output for a long time.

Numerous samples of the gas sensing element according to the first embodiment were fabricated to test the durability of each sensing element against poisonous Si components.

More specifically, to evaluate the Si poisoning durability, the fabricated gas sensing elements were differentiated in various factors, such as an average particle diameter RB ($\mu$m) of the coarse particles, material B of the coarse particles, a specific surface SA[B] (m$^2$/g) of the coarse particles, an average particle diameter RA ($\mu$m) of the fine particles, material A of the fine particles, a specific surface SA[A] (m$^2$/g) of the fine particles, a weight ratio WA/W, and a thickness (um) of the protective layer. W is a sum of WA and WB, where WA represents an amount of the fine particles contained in the protective layer and WB represents an amount of the coarse particles contained in the protective layer.

The average particle diameter RA of the fine particles was in the range from 0.1 $\mu$m to 5 $\mu$m. The specific surface SA[A] of the fine particles was in the range from 2 m$^2$/g to 100 m$^2$/g. The material A of the fine particles was $\gamma$-Al2O3 or $\alpha$-Al2O3. The average particle diameter RB of the coarse particles was 15 $\mu$m. The specific surface SA[B] of the coarse particles was 2 m$^2$/g or 100 m$^2$/g. The material B of the coarse particles was $\alpha$-Al2O3 or $\gamma$-Al2O3. The weight ratio WA/W was in the range from 10% to 100%. The thickness of the protective layer was in the range from 20 $\mu$m to 200 $\mu$m.

The durability against Si poisoning was evaluated by a change rate of the sensor output before and after the accelerated poisoning test. The sample indicated by ⊙ has shown the change rate less than 10%. The sample indicated by ○ has shown the change rate in the range from 10% to 20%. The sample indicated by X has shown the change rate equal to or larger than 20%.

To conduct the durability test, an in-line four cylinder engine of 2,000 cc equipped with a fuel injector was continuously driven at the speed of 3,000 r.p.m. while the tested element sample was kept at the temperature of 600° C.

The gasoline used for the durability test contains Si oil (dimethylsiloxane) of 0.5 cc per liter. The durability test was conducted for 200 hours.

The sensor output was measured at the timing of $\lambda$=0.95 during the depiction of an output waveform responsive to a continuous change from $\lambda$=0.9 to $\lambda$=1.1.

To conduct the measurement of the sensor output, an in-line six cylinder engine of 2,000 cc equipped with a fuel injector was driven at the speed of 1,100 r.p.m. while nonleaded gasoline was supplied to the fuel injector.

The test result is shown in Table 1.

According to Table 1, each of samples 15 and 16 has a protective layer made of only fine particles. The protective layer of sample 15 is thin. Sample 16 causes numerous cracks in the process of forming the protective layer. Thus, samples 15 and 16 are insufficient in the durability against poisonous substances.

Sample 8 has a protective layer made of only $\alpha$-Al2O3 (i.e., a hexagonal system). Therefore, sample 8 has coarse particles whose specific surface is small and cannot obtain a satisfactory durability against Si poisoning.

Sample 12 has a protective layer having a small weight ratio WA/W (i.e., WA/W=20). According to sample 12, the interparticle cavities between the coarse particles were not sufficiently filled with the fine particles. Thus, sample 12 cannot obtain a satisfactory Si poisoning durability.

Other samples have protective layers basically consisting of coarse particles and fine particles. The fine particles are made of $\gamma$-Al2O3 whose specific surface is large, and therefore these samples can obtain satisfactory durability against Si poisoning. Regarding sample 9, the coarse particles are made of $\gamma$-Al2O3 and the durability against Si poisoning was satisfactory.

Furthermore, it was confirmed that any samples satisfying the following conditions cause no deterioration in the sensor output and show excellent durability against Si poisoning, wherein the requisite conditions are: RB/RA is equal to or larger than 7.5; the fine particles have specific surface equal to or larger than 50 m$^2$/g; WA/W is equal to or larger than 20; and the thickness of the protective layer is equal to or larger than 50 $\mu$m. For example, each of samples 1-5, 7, 10, 11, 13, and 14 satisfies the requisite conditions.

TABLE 1

| No. | 1 | 2 | 3 | 4 | 5 | 6 | 7 | 8 |
|---|---|---|---|---|---|---|---|---|
| RA ($\mu$m) | 0.1 | 0.2 | 0.3 | 1 | 2 | 5 | 0.2 | 0.2 |
| RB ($\mu$m) | 15 | 15 | 15 | 15 | 15 | 15 | 15 | 15 |
| RB/RA | 150 | 75 | 50 | 15 | 7.5 | 3 | 75 | 75 |
| WA/W (%) | 30 | 30 | 30 | 30 | 30 | 30 | 30 | 30 |
| fine particle material A | $\gamma$-Al$_2$O$_3$ | $\gamma$-Al$_2$O$_3$ | $\gamma$-Al$_2$O$_3$ | $\gamma$-Al$_2$O$_3$ | $\gamma$-Al$_2$O$_3$ | $\gamma$-Al$_2$O$_3$ | $\gamma$-Al$_2$O$_3$ | $\alpha$-Al$_2$O$_3$ |

TABLE 1-continued

| | | | | | | | | |
|---|---|---|---|---|---|---|---|---|
| SA[A] (m²/g) coarse particle material B | 100 | 100 | 100 | 100 | 100 | 100 | 50 | 2 |
| | α-Al₂O₃ | α-Al₂O₃ | α-Al₂O₃ | α-Al₂O₃ | α-Al₂O₃ | α-Al₂O₃ | α-Al₂O₃ | α-Al₂O₃ |
| SA[B] (m²/g) | 2 | 2 | 2 | 2 | 2 | 2 | 2 | 2 |
| thickness (μm) | 100 | 100 | 100 | 100 | 100 | 100 | 100 | 100 |
| Si poisoning durability | ⊚ | ⊚ | ⊚ | ⊚ | ⊚ | ○ | ⊚ | X |

| No. | 9 | 10 | 11 | 12 | 13 | 14 | 15 | 16 |
|---|---|---|---|---|---|---|---|---|
| RA (μm) | 0.2 | 0.2 | 0.2 | 0.2 | 0.2 | 0.2 | 0.2 | 0.2 |
| RB (μm) | 15 | 15 | 15 | 15 | 15 | 15 | — | — |
| RB/RA | 75 | 75 | 75 | 75 | 75 | 75 | — | — |
| WA/W (%) | 30 | 30 | 30 | 10 | 20 | 50 | 100 | 100 |
| fine particle material A | α-Al₂O₃ | γ-Al₂O₃ | γ-Al₂O₃ | γ-Al₂O₃ | γ-Al₂O₃ | γ-Al₂O₃ | γ-Al₂O₃ | γ-Al₂O₃ |
| SA[A] (m²/g) | 10 | 100 | 100 | 100 | 100 | 100 | 100 | 100 |
| coarse particle material B | γ-Al₂O₃ | α-Al₂O₃ | α-Al₂O₃ | α-Al₂O₃ | α-Al₂O₃ | α-Al₂O₃ | — | — |
| SA[B] (m²/g) | 100 | 2 | 2 | 2 | 2 | 2 | — | — |
| thickness (μm) | 100 | 50 | 200 | 100 | 100 | 100 | 20 | 100 |
| Si poisoning durability | ⊚ | ⊚ | ⊚ | X | ⊚ | ⊚ | X | X |

Second Embodiment

Figure 5:
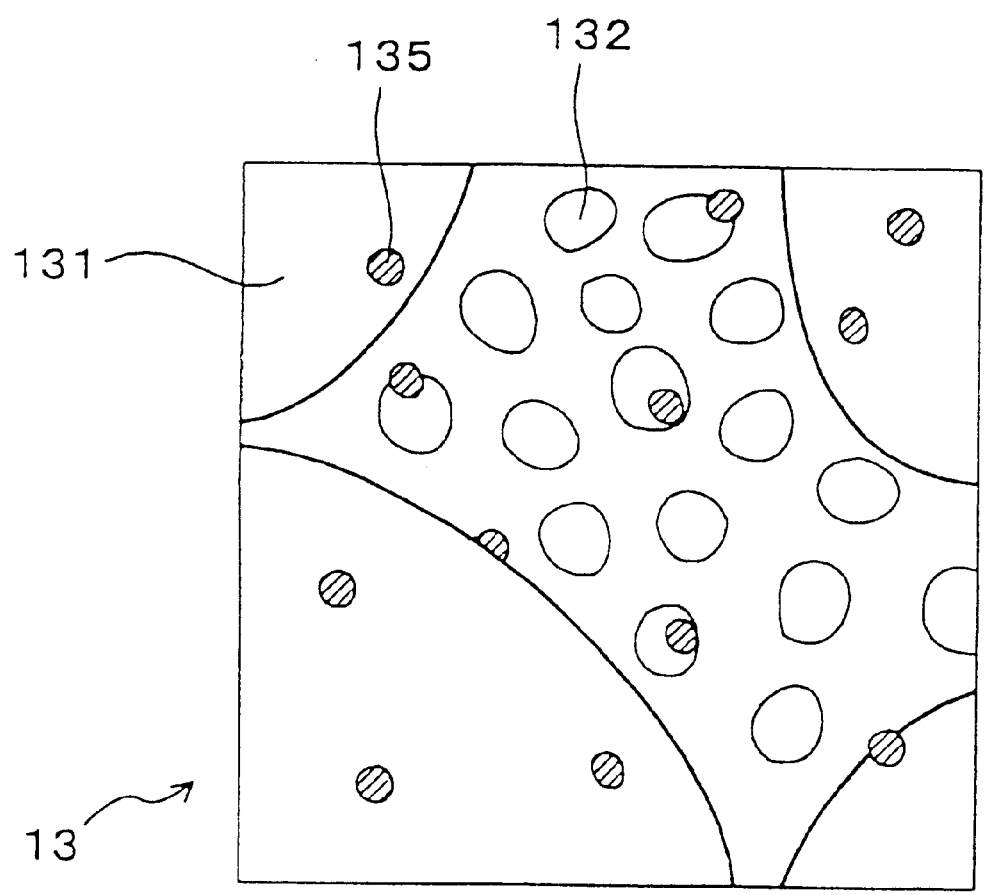
FIG. 5 is an enlarged view showing details of a second protective layer in accordance with a second embodiment of the present invention.

A second embodiment of the present invention is a gas sensing element whose protective layer contains a noble metallic catalyst as shown in FIG. 5.

The gas sensing element of the second embodiment is structurally similar to the gas sensing element of the first embodiment.

More specifically, the gas sensing element 1 of this embodiment comprises the solid electrolytic body 10 having an oxygen ionic conductance, the reference gas sensing electrode 11, and the measured gas sensing electrode 12 which cooperatively constitute an electrochemical cell. Air, serving as the reference gas, is introduced in the cup-shaped solid electrolytic body 10. An electric potential difference, representing an oxygen concentration difference between the reference gas and the measured gas, is produced between the gas sensing electrode 11 and the measured gas sensing electrode 12. In this respect, the gas sensing element 1 is a cell producing an electromotive force representing an air-fuel ratio of the measured gas.

Furthermore, the surface of the measured gas sensing electrode 12 is covered by the first protective layer 130. The second protective layer 13 covers the outer surface of the first protective layer 130. The inside space of the solid electrolytic body 10 defines the reference gas chamber 100 which is filled with air (refer to FIG. 1).

As shown in FIG. 5, the second protective layer 13 of this embodiment comprises the coarse particles 131 and the fine particles 132. Catalytic particles 135 made of Pt are held on the surfaces of the coarse particles 131 and the fine particles 132.

Like the measured gas sensing electrode, the catalytic particles 135 have a function of equilibrating the natural gas and therefore stabilizes the sensor output. Due to these functions, the catalytic particles 135 can assist or improve the ability of trapping Si or similar poisonous gaseous substances in the protective layer.

The protective layer of this embodiment was fabricated in the following manner.

Water, inorganic binder and dispersant were added to the mixture of the coarse particles and the fine particles to fabricate a slurry. The weight percentage of inorganic binder relative to all of the particles is 3 to 10 wt %. This slurry was applied or coated on the surfaces of the solid electrolytic body and the measured gas sensing electrode by dipping or spraying. Thereafter, the slurry was baked at the temperature range from 500° C. to 900° C. to obtain the protective layer.

Furthermore, water solution of Pt salt was applied on the baked gas sensing element 1 by dipping. Thus, the protective layer was saturated with Pt salt and then dried.

Thereafter, the gas sensing element was baked at the temperature range from 500° C. to 900° C. to settle Pt in the protective layer.

The amount of Pt contained in the protective layer can be adjusted by changing the concentration of Pt salt in the solution.

The rest of the second embodiment is similar to that of the first embodiment.

A plurality of samples of the gas sensing element according to the second embodiment were prepared to test the durability against Si poisoning and initial response of each sensing element.

More specifically, to evaluate the Si poisoning durability, the prepared gas sensing elements were differentiated in various factors, such as an average particle diameter RA (μm) of the fine particles, material A of the fine particles, a specific surface SA[A] (m²/g) of the fine particles, and a content of Pt (wt %) relative to the protective layer, as shown in Table 2.

Other properties of the tested samples are not differentiated. The average particle diameter RB of the coarse particles was 15 μm. The material B of the coarse particles is α-Al2O3. The specific surface SA[B] of the coarse particles was 2 m²/g. The weight ratio WA/W in the mixture of the coarse particles and the fine particles was 30%. The thickness of the protective layer was 100 μm.

The durability against Si poisoning was evaluated by the same method as that employed in the first embodiment. The sample indicated by ⊚ has shown the change rate less than 5%. The sample indicated by ○ has shown the change rate in the range from 5% to 20%. The sample indicated by X has shown the change rate equal to or larger than 20%.

The initial response was measured based on a gas response time required for the sensor output to change from 0.6 V to 0.3V in response to the switching from $\lambda=0.9$ to $\lambda=1.0$. To conduct the measurement of the initial response, an in-line six cylinder engine of 2,000 cc equipped with a fuel injector was driven at the speed of 1,100 r.p.m. while nonleaded gasoline was supplied to the fuel injector.

The sample indicated by ○ has shown the gas response time less than 150 ms. The sample indicated by Δ has shown the gas response time in the range from 150 ms to 200 ms. The sample indicated by X has shown the gas response time equal to or larger than 200 ms.

The test result is shown in Table 2.

According to Table 2, sample 23 has a protective layer consisting of the fine particles and the coarse particles both being made of α-Al2O3. In other words, sample 23 has a small specific surface and therefore has insufficient durability against Si poisoning.

Furthermore, it was confirmed that increasing the Pt content up to 10% worsened the initial response although the durability against Si poisoning was improved.

TABLE 2

| No. | 2 | 17 | 18 | 19 | 20 | 21 | 22 | 23 |
|---|---|---|---|---|---|---|---|---|
| RA (μm) | 0.2 | 0.2 | 0.2 | 0.2 | 0.2 | 0.2 | 0.2 | 0.2 |
| fine particle material A | γ-Al$_2$O$_3$ | γ-Al$_2$O$_3$ | γ-Al$_2$O$_3$ | γ-Al$_2$O$_3$ | γ-Al$_2$O$_3$ | γ-Al$_2$O$_3$ | γ-Al$_2$O$_3$ | α-Al$_2$O$_3$ |
| SA[A] (m$^2$/g) | 100 | 100 | 100 | 100 | 100 | 100 | 100 | 2 |
| Pt content (wt %) | 0 | 0.1 | 0.2 | 0.5 | 1 | 5 | 10 | 0.5 |
| Si poisoning durability | ○ | ○ | ⊚ | ⊚ | ⊚ | ⊚ | ⊚ | X |
| initial response | ○ | ○ | ○ | ○ | ○ | ○ | X | ○ |

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensing element comprising a solid electrolytic body, a reference gas sensing electrode provided on a surface of said solid electrolytic body so as to be exposed to a reference gas, a measured gas sensing electrode provided on another surface of said solid electrolytic body so as to be exposed to a measured gas, wherein a ceramic porous protective layer is provided on a surface of said measured gas sensing electrode, said protective layer comprises coarse particles and fine particles structurally arranged in such a manner that interparticle cavities formed between said coarse particles are filled with said fine particles wherein said protective layer satisfies a relationship that a ratio RB/RA is equal to or larger than 3, where RA represents an average particle diameter of said fine particles while RB represents an average particle diameter of said coarse particles, and at least one of said coarse particles and said fine particles contain at least one selected from the group consisting of γ-Al2O3, θ-Al2O3, δ-Al2O3 and solid solution having the same crystal structure as those of γ-Al2O3, θ-Al2O3, δ-Al2O3, and the other one of said fine and coarse particles is α-Al2O3.

2. The gas sensing element in accordance with claim 1, wherein said protective layer contains a noble metallic catalyst.

3. The gas sensing element in accordance with claim 1, wherein an average particle diameter of said fine particles is in a range from 0.1 μm to 5 μm and an average particle diameter of said coarse particles is in a range from 0.3 μm to 50 μm.

4. The gas sensing element in accordance with claim 1, said protective layer satisfies a relationship that a weight ratio WA/W is equal to or larger than 20, wherein W is a sum of WA and WB, WA represents an amount of said fine particles contained in said protective layer and WB represents an amount of said coarse particles contained in said protective layer.

5. A gas sensing element comprising a solid electrolytic body, a reference gas sensing electrode provided on a surface of said solid electrolytic body so as to be exposed to a reference gas, a measured gas sensing electrode provided on another surface of said solid electrolytic body so as to be exposed to a measured gas, wherein a ceramic porous protective layer is provided on a surface of said measured gas sensing electrode, said protective layer comprises coarse particles and fine particles arranged in such a manner that interparticle cavities formed between said coarse particles are filled with said fine particles wherein said protective layer satisfies a relationship that a ratio RB/RA is equal to or larger than 3, where RA represents an average particle diameter of said fine particles while RB represents an average particle diameter of said coarse particles, and at least one of said coarse particles and said fine particles have a specific surface equal to or larger than 50 m$^2$/g, and the other one of said fine and coarse particles has a specific surface less than 50 m$^2$/g.

6. A gas sensing element comprising a solid electrolytic body, a reference gas sensing electrode provided on a surface of said solid electrolytic body so as to be exposed to a reference gas, a measured gas sensing electrode provided on another surface of said solid electrolytic body so as to be exposed to a measured gas, wherein a ceramic porous protective layer is provided on a surface of said measured gas sensing electrode, said protective layer comprises first particles and second particles mixed with each other so as to be structurally arranged in such a manner that interparticle cavities formed between said first particles are filled with said second particles, and at least one of said first particles and said second particles contain at least one selected from the group consisting of γ-Al2O3, θ-Al2O3, δ-Al2O3 and solid solution having the same crystal structure as those of γ-Al2O3, θ-Al2O3, δ-Al2O3, and the other one of said first and second particles is α-Al2O3.

7. The gas sensing element in accordance with claim 6, wherein said protective layer contains a noble metallic catalyst.

8. The gas sensing element in accordance with claim 6, wherein said protective layer satisfies a relationship that a ratio RB/RA is equal to or larger than 3, where RA represents an average particle diameter of said second particles while RP represents an average particle diameter of said first particles.

9. The gas sensing element in accordance with claim 6, wherein an average particle diameter of said second particles is in a range from 0.1 μm to 5 μm and an average particle diameter of said first particles is in a range from 0.3 μm to 50 μm.

10. The gas sensing element in accordance with claim 6, said protective layer satisfies a relationship that a weight ratio WA/W is equal to or larger than 20, wherein W is a sum of WA and WB, WA represents an amount of said second particles contained in said protective layer and WB represents an amount of said first particles contained in said protective layer.

11. A gas sensing element comprising a solid electrolytic body, a reference gas sensing electrode provided on a surface of said solid electrolytic body so as to be exposed to a reference gas, a measured gas sensing electrode provided on another surface of said solid electrolytic body so as to be exposed to a measured gas, wherein a ceramic porous protective layer is provided on a surface of said measured gas sensing electrode, said protective layer comprises first particles and second particles mixed with each other so as to be arranged in such a manner that interparticle cavities formed between said coarse particles are filled with said second particles, and at least one of said coarse particles and said fine particles have a specific surface equal to or larger than 50 m$^2$/g, and the other one of said fine and coarse oarticles has a specific surface less than 50 m$^2$/g.

* * * * *